United States Patent [19]

Peyman et al.

[11] Patent Number: 4,633,866

[45] Date of Patent: Jan. 6, 1987

[54] OPHTHALMIC LASER SURGICAL METHOD

[76] Inventors: Gholam Peyman, 535 N. Michigan Ave., Chicago, Ill. 60611; Esa Viherkoski, Kuusmiehentie 56 G, 00670 Helsinki 67, Finland

[21] Appl. No.: 370,696

[22] Filed: Apr. 22, 1982

[30] Foreign Application Priority Data

Nov. 23, 1981 [FI] Finland ................................. 813736

[51] Int. Cl.⁴ .............................................. A61N 5/06
[52] U.S. Cl. .................................. 128/303.1; 128/395
[58] Field of Search ....................... 128/303.1, 395–398

[56] References Cited

U.S. PATENT DOCUMENTS

| | | | |
|---|---|---|---|
| 3,884,236 | 5/1975 | Krasnov | 128/303.1 |
| 3,971,382 | 7/1976 | Krasnov | 128/303.1 |
| 4,309,998 | 1/1982 | Aron et al. | 128/303.1 |
| 4,391,275 | 7/1983 | Frankhauser et al. | 128/303.1 |

OTHER PUBLICATIONS

Vassiliadis, "Photocoagulation Source Technology and Ocular Effects", Ch. 2, pp. 5–38, *Ocular Photocoagulation* (1975).

L'Esperance, *Ocular Photocoagulation*, pp. 227–229, 285–297, 315–318, 1975.

Boettner et al., "Transmission of the Ocular Media", Investigative Opthalmology 6, pp. 776–783, 1962.

Fuller et al., "Carbon Dioxide Laser Surgery of the Eye", pp. 214–225.

Van der Zyphen et al., "On the Effects of Different Laser . . . ", Int. Ophtholy 1, pp. 39–48, 1978.

Goldman et al., "Ocular Damage Thresholds . . . ", Exp. Eye Res., 24, pp. 45–56, 1977.

Marshall, "Thermal and Mechanical Mechanisms . . . Retina", 9, Investigative Ophthalmology 2, pp. 97–115, Feb. 1970.

Van der Zyphen et al., "Changes in the Ultrastructure . . . ", 39, Adv. Ophthal., pp. 59–180, 1979.

Stefani et al., "Q-Switched Rubylaser . . . ", Graefes Archiv Ophthalmologie, pp. 49–55, 1978.

Aron-Rosa et al., "Applications . . . Yag Pulses", J. Fr. Ophthalmol, 4, 1, pp. 61–66, 1981.

Vaughn et al., General Ophthalmology, Ch. 8, 12, 1977.

Goldman, "Some Current Developments . . . Surgery", Laser Surgery, pp. 11–18, 1976.

Frankhauser et al., "Clinical Studies . . . of the Eye", Int. Ophthal. 3, 3, pp. 129–139, 1981.

Dannheim et al., Laser Lesions . . . Eye", 205 Graefes Archiv Ophthalmologie, pp. 175–205, 1978.

*Primary Examiner*—Lee S. Cohen
*Attorney, Agent, or Firm*—Thomas A. Kmiotek

[57] ABSTRACT

An ophthalmic laser surgical method for treating or removing intraocular tissue anterior to the fundus while reducing the likelihood of photocoagulation damage to the fundus. Laser radiation in the infrared wavelength range is directed at the tissue to be treated or removed, the wavelength range being selected so as to minimize transmission of the laser radiation to the fundus by the ocular structures anterior to the retina.

16 Claims, No Drawings

OPHTHALMIC LASER SURGICAL METHOD

FIELD OF THE INVENTION

This invention relates generally to a method of treating intraocular tissues and of removing intraocular membranes by directing laser radiation into the eye. In particular, it relates to a method of performing surgical laser treatments of the eye without causing substantial damage to the fundus.

BACKGROUND OF THE INVENTION

The light absorption and light transmission characteristics of the tissues and fluids of the eye have been the subjects of study for a number of years. By means of various spectroscopic measuring devices, the absorption and transmission by the parts of the eye of light of a wide range of wavelengths have been determined with accuracy sufficient to permit reproduction of the results.

In order to produce light of a range of wavelengths, from the ultraviolet range through the infrared range, mercury vapor, xenon arc, halogen and laser light sources, among others, have been employed. These light sources were then utilized to determine the specific wavelength ranges in which the individual eye parts absorbed or transmitted light.

Among the findings of these studies was the finding that the transmission of ultraviolet light by the frontal portions of the eyes decreases with age, while the transmission of infrared light by those same portions of the eyes was essentially independent of age.

The use of laser light in ophthalmic treatments is a relatively recent development growing out of such studies, one which began in about 1965 with the use of the ruby laser. The use of the argon laser in ophthalmology began shortly thereafter, followed by the advent of the neodymium-doped yttrium-aluminum garnet laser (commonly known as the Nd:YAG laser).

Both the argon laser and the Nd:YAG have recently been utilized in numerous ophthalmic surgical procedures, among them the treatment of glaucoma and cataracts. With respect to treatment of the former condition, one procedure has involved directing a short, strong laser pulse through the pupil so as to form a hole between the anterior and posterior chambers, thereby equalizing intraocular pressure. In another procedure, a laser pulse aimed at the trabecular meshwork is utilized to open a blocked duct to the canal of Schlemm. Alternatively, the laser pulse is used to make a small mark in the trabecular meshwork, which, in the process of scar formation, pulls the surrounding tissue toward the mark. This tissue stretching causes the small ducts and canals of that region to open into the canal of Schlemm, thus restoring the circulation of fluid within the eye.

Other surgical procedures employing laser light are of great importance. Among them are the opening of the lens capsule and the breaking of membranes in the vitreous. With respect to the latter, it is well-known that capsular opacification is the major complication which occurs after extracapsular extraction of the lens and insertion of a posterior chamber implant. While meticulously clearing and polishing the posterior capsule reduce capsular opacification to some degree, the condition is never fully eliminated. Previous treatment of this secondary membrane condition has been accomplished by capsulotomy with a cytotome or knife, or, when the membranes are thick, by pars planar membranectomy. Both of these procedures require substantial intraocular manipulation and both therefore create the risk of intraocular infection or retinal detachment. Accordingly, the use of a laser as a non-invasive method of managing such secondary membranes is highly desirable. For the same reasons, it is desirable to disrupt other types of membranes, such as those which form behind other intraocular implants, by means of laser treatment.

A danger present in each of the laser surgical procedures discussed above, is that the laser light will penetrate beyond the tissues desired to be treated and will be transmitted to the retina where undesirable photocoagulation damage will occur. This is particularly true in the case of capsulotomies and in the case of the breaking of occluding membranes, whether pupillary or vitreous, wherein the laser beam is directed along the visual axis. In these cases, any damage to the fundus results in permanent vision impairment. Therefore, essentially no risk is tolerable in such procedures.

Thus, an important limitation is placed on the scope of use of ophthalmic laser treatments i.e., the need to avoid any substantial laserinduced damage to the fundus.

BRIEF DESCRIPTION OF THE PRIOR ART

It is well documented in the prior art that, unless precautionary measures are taken, laser surgical treatment of the anterior structures of the eye may result in substantial damage to the fundus. The extent to which such damage occurs is, of course, dependent upon the type of laser utilized, since each type emits a different wavelength and since different portions of the eye possess different light transmission and absorption characteristics.

The particular absorption and transmission characteristics of each distinct ocular structure were extensively studied by Boettner et al. in their paper entitled "Transmission Of The Ocular Media", published at pp. 776–783 of 1 *Investigative Ophthamology* 6 (December 1962). Boettner et al. found that the eye as a whole transmitted a significant percentage of light in the range from the ultraviolet (wavelengths of 300 nanometers and above) through the near infrared (wavelengths of up to about 2200 nanometers). Each structure of the eye, however, had one or more significant absorption bands corresponding to those of water.

With respect to the individual ocular structures, the findings were as follows: (1) Cornea—good transmittance throughout the studied range, but with sharp absorption bands at 1430 nanometers and at 1950 nanometers. (2) Aqueous humor—good transmittance from about 280 nanometers to about 1400 nanometers, with identifiable absorption bands at 980 nanometers and at 1200 nanometers. The aqueous has less than 1% transmittance from 220 to 260 nanometers, and reaches a level of only approximately 18% transmittance between about 1500 nanometers and about 1900 nanometers. There is virtually no transmittance beyond the absorption band at about 1950 nanometers. (3) Lens—range of transmission is from about 310 nanometers to about 1900 nanometers. Sharp absorption bands exist at about 360 nanometers and at about 1430 nanometers, while other identifiable bands occur at 980 nanometers and at 1200 nanometers. Transmission is quite high in the wavelength range from about 400 nanometers to about 1400 nanometers. (4) Vitreous humor—range of transmission is from about 300 nanometers to about 1450 nanometers, with a sharp absorption band at about 980 nanometers and an identifiable band at about 1200 nanometers. The transmission of the vitreous falls off sharply beginning at about 1100 nanometers.

Vassiliadis, "Photocoagulation Source Technology And Ocular Effects", ch. 2, pp. 5–19 of *Ocular Photocoagulation* (1975), teaches the desirability of using a laser having an output wavelength which is transmitted well by all the ocular media and is absorbed well by the target structure in those instances when it is the object of the procedure to produce photocoagulation effects in the fundus. This reference further notes that laser light sources generating wavelengths in the infrared region are of no utility for that purpose because of their absorption by water in the ocular media.

Yet where the object is to treat ocular structures anterior to the fundus, photocoagulation of the retina or its associated structures is highly undesirable. L'Esperance, *Ocular Photocoagulation*, (1975), ch. 14, "Complications", relates the effects of the penetration of an argon laser beam (having wavelengths of 457.9, 488.0 and 514.5 nanometers) to structures posterior to those desired to be treated. In performing argon laser treatments of the cornea, for example, it has been found that an area having an endothilial haze will require increased power to effect the treatment. When, however, the beam is then moved from such an area to another not having such a haze, the penetration of the beam will be such as to render retinal or choroidal rupture possible. This same danger may arise when it is the lens which is being treated, for an area of opacification of the lens will require a similar increase in the power delivered to the affected area in order to successfully complete the treatment. This power increase will similarly increase the likelihood of damage to the fundus in the event of a deflection or movement of the beam. Such dangers are also present when it is desired to effect laser treatment of the vitreous whenever blood cells or other debris is present therein.

Similarly, Stefani et al., "Q-Switched Ruby Laser Induced Damage Of The Adult Rabbit Lens Capsule", *Graefes Arch. klin. exp. Ophthal.* 206, 49–55 (1978), reported that an observed side-effect or complication arising from inducing rupture of the anterior lens capsule with a ruby laser was a very serious one, i.e., retinochoroidal rupture with localized preretinal hemorrhage.

Parallel findings have been recorded with respect to the use of the Nd:YAG laser (wavelength 1064 nanometers) in treatments of the iris in Roper-Hall et al., eds., *Advances In Ophthalmology*, Vol. 39 (1979), pp. 68–69. It is noted in this reference that precautionary measures are necessary to prevent retinal, corneal or lenticular damage when treating the iris with various types of lasers. In particular, it is taught that, in order to protect the retina, one must exactly focus the beam upon the treatment area and must insure that there is an oblique incidence of the beam upon the iris. The experimental procedure described, namely, the directing of a series of stepped energy increase Nd:YAG laser pulses at the iris, resulted in heavy chorio-retinal damage even at the lower to middle energy ranges.

Goldman et al., "Ocular Damage Thresholds And Mechanisms For Ultrashort Pulses Of Both Visible And Infrared Laser Radiation In The Rhesus Monkey", *Exp. Eye Res.* 24, 45–56 (1977), have reported, however, that there is no significant difference between the type of retinal damage produced by different exposure diameters at the Nd:YAG wavelength of 1064 nanometers. This retinal damage has been characterized by Marshall, "Thermal And Mechanical Mechanisms In Laser Damage To The Retina," *Investigative Ophthalmology*, pp. 97–115 (February 1970), as resulting from both the thermal and mechanical effects of the beam striking the retina. Marshall further observed that absorption of the beam by melanin granules appeared to be responsible for these effects.

Other evidence of the need to prevent the penetration side-effects of laser treatments of ocular structures is documented by Fuller et al., *Carbon Dioxide Laser Surgery Of The Eye*, pp. 214–225, who noted that a previous study involving $CO_2$ laser penetration of the sclera resulted in damage to the lens and to the cornea. Nonetheless, Fuller et al. teach the use of the $CO_2$ laser for treatment of tissues anterior to the anterior chamber, stating that the aqueous is opaque to the $CO_2$ laser beam and acts as a barrier to further intraocular penetration by the beam.

As reported by a number of investigators, substantial damage to the fundus is likely when laser devices are utilized in an effort to treat the anterior portions of the eye. Laser energy which penetrates the treated structures during the procedure is transmitted to the fundus by the intermediate ocular tissues, thereby causing injury from undesired photocoagulation. This danger is present when any of the three most widely used laser sources, namely the argon laser with its wavelengths in the visible range (i.e., 457.9, 488.0 and 514.5 nanometers), the ruby laser which also emits in the visible range (i.e., at 695.0 nanometers), and the Nd:YAG laser with its wavelength in the near infrared range (i.e., 1064 nanometers), are used for laser surgical treatments, as reported by Van der Zypen, "On The Effects Of Different Laser Energy Sources Upon The Iris Of The Pigmented And The Albino Rabbit", *Int. Ophthalmology*, 1,1:39–48 (1978). The danger of injury to the fundus is, as previously noted, known to be particularly great when these lasers are utilized for capsulotomies or for disrupting other intraocular membranes.

That severe retinal damage is caused by laser radiation in the infrared wavelength range, i.e., by the Nd:YAG laser emitting at 1064 nanometers, is therefore widely reported, despite the suggestions of some investigators, notably Boettner et al. and Vassiliadis, that such laser energy would not penetrate the eye sufficiently to cause photocoagulation. Accordingly, the dangers inherent in the ophthalmic surgical use of lasers emitting in the near infrared range are well-known.

SUMMARY OF THE INVENTION

In order to reduce and prevent damage to the fundus during laser surgery involving tissues and membranes of the eye anterior to the retina, a new ophthalmic surgical method is provided which comprises treating the desired area by exposing it to laser light having a wavelength such that at least about 80% or more of the laser light penetrating the treatment area is absorbed by the vitreous before it can reach and damage the retina. Thus, the method of the invention permits known laser surgical procedures to be performed with much greater safety to the retina and its associated structures.

The laser light to be utilized in the new method of the invention is in the near infrared range. In particular, we have found that laser light having a wavelength of from about 1100 nanometers to about 1350 nanometers, or having a wavelength of between about 1850 nanometers and about 2050 nanometers, would be suitable for this purpose. In these wavelength ranges the transmission of the cornea is as high as 80%, the transmission of the aqueous humor is as high as 70%, and the transmission of the lens is as high as 70%. The vitreous humor, however, transmits a maximum of from about 5% to about 8% of the laser light at these frequencies.

The preferred wavelength range for the laser light used in the present invention is from about 1100 nanometers to about 1350 nanometers. Laser radiation in this range is particularly useful for performing membrane disruption procedures, although the precise wavelength to be used depends upon the location and nature of the membrane. Laser light having wavelengths of from about 1100 nanometers to about 1200 nanometers is useful for disrupting pupillary membranes and for disrupting membranes or other floating tissue in the vitreous. While use of the laser in this wavelength range reduces the risk of damage to the cornea, there remains some danger of retinal damage, but not such danger as could not be easily avoided by proper aiming techniques. At these wavelengths approximately 70% to 80% of the laser energy is absorbed prior to reaching the retina. Thus, proper aiming may produce the desired treatments with minimal retinal damage.

When laser radiation having a wavelength of about 1300 nanometers (1300–1310 nanometers) is utilized in membrane disruption procedures, however, the retina cannot be damaged even if the laser beam is focused upon it. Most preferably, therefore, the method of the invention is carried out by utilizing an Nd:YAG laser source emitting radiation at a wavelength in the range of from about 1300 nanometers to about 1310 nanometers. A device found particularly useful for this purpose is the mode-locked "P/V YAG" laser, manufactured by Laser Tek OY, a corporation of Finland, which emits radiation in this most preferred wavelength range. Accordingly the method of the present invention permits a minimum amount of the laser radiation to penetrate to the fundus, and the danger of damage to the retina and its associated structures is therefore greatly reduced or even eliminated entirely. Moreover, by eliminating the need to employ numerous and awkward precautionary measures, the method of the invention enables the surgeon to choose the energy and location of the laser impacts so as to most effectively treat the desired area, rather than compromise that effectiveness out of concern for causing other damage.

The laser light utilized in the invention is preferably directed into the eye by means of a mirror (articulating) arm or by means of an optic fiber, or by other well-known means.

It is also preferable that the laser light source be equipped to generate pulsed laser light having a pulse duration of from about 10 to about 50 nanoseconds, each pulse delivering energy in the range of from about 100 milli-Joules to about 150 milli-Joules.

Accordingly, it is an object of the present invention to provide a method of treating anterior portions of the eye by laser radiation having a wavelength which substantially reduces the danger of injuring the fundus with that portion of the laser radiation which may otherwise penetrate the treatment area.

A further object of the invention is to provide a method of laser treatment or membrane disruption which permits the surgeon to effectively treat the desired area without being required to compromise that treatment (e.g., to change the angle of incidence of the laser beam) in order to avoid causing unwanted photocoagulation injury to the fundus.

Other objects and advantages of the invention will be apparent to those skilled in the art from the following detailed description and claims.

DETAILED DESCRIPTION

Set forth in the following discussion are summaries of a number of laboratory and animal studies demonstrating the principles of the present invention.

Preliminary Evaluations

1. An infrared spectrophotometer was used to evaluate the transmission characteristics of the cornea, the aqueous, the lens and the retina. These characteristics were compared with those of normal saline and with those of water. These studies were conducted in an attempt to confirm the findings of Boettner et al. discussed above.

Virtually all of the studied materials showed a band of absorption between about 1300 nanometers and about 1500 nanometers. Another absorption peak was observed at about 1900 nanometers. From these results it was concluded that neither the proteins present in cornea and lens tissue nor hyaluronic acid played an important role in determining infrared absorption. It appears, instead, that the water content of ocular media and the thickness of the water-containing structures are the determinative factors in near-infrared absorption.

2. In choosing the wavelengths at which clinical studies involving the Nd:YAG laser treatments were to be carried out, the published infrared absorption characteristics of methyl methacrylate were considered, inasmuch as intraocular prosthetic lenses are commonly made of this material. Data published by a principal manufacturer of this material, Rohm & Haas Company, indicated that there an absorption minimum existed at about 1300 nanometers, while an absorption maximum (absorption=40–50%) appeared at about 1800 nanometers. Because a principal use of the Nd:YAG laser described herein is to perform capsulotomies, i.e., rupture of secondary membranes subsequent to extracapsular extraction of the lens, and because intraocular lenses are frequently implanted after such extractions, it was decided to conduct further work with laser light wavelengths in the region of about 1300 nanometers.

Equipment

As previously discussed, the commonly-available Nd:YAG laser emits light at a wavelength of 1064 nanometers. As also previously discussed, laser light of this wavelength is of great utility in disrupting membranes, but is capable of producing serious injury to the retina.

In order to conduct studies in the desired 1300–1310 nanometer wavelength range, it was necessary to utilize the Nd:YAG laser apparatus manufactured by Laser Tek OY, a corporation of Finland. This device is known as the "P/V YAG" laser, and emits light in the desired wavelength range of 1300–1310 nanometers (hereinafter simply referred to as a wavelength of 1300 nanometers). It is capable of producing a pulsed laser beam having a pulse energy of 120 milli-Joules and a pulse duration of 40 nanoseconds. A series of from one to ten pulses may be emitted from the apparatus. The beam emitted from the apparatus was focused by using either a Zeiss slit lamp (beam diameter 50 microns) or a +20 diopter lens (beam diameter 200 microns). Additionally, it has been found useful to employ so-called "mode-locking" in the laser apparatus in order to keep the focal point of the beam steady and to eliminate so-called "side-beams" of undesired wavelengths.

All personnel involved in these studies were provided with infrared absorbing goggles.

Experiment #1

Wavelength Comparison

Two Nd:YAG lasers were employed in this study; one emitting at 1064 nanometers, the other at 1300 nanometers.

In this study, pigmented and non-pigmented rabbit eyes were irradiated while the rabbits were under general anesthesia and while their pupils were dilated. This was accomplished by directing an unfocused laser beam into the eyes for various time intervals up to five minutes in length.

Neither laser produced any lesion in non-pigmented rabbit eyes, even after the maximum exposure time. On the other hand, large retinal photocoagulation effects were observed in the pigmented eyes when irradiated with the laser emitting at the 1064 nanometer wavelength. It was found to be impossible to induce any retinal lesion with the P/V YAG laser, emitting at a wavelength of 1300 nanometers, regardless of the exposure time.

This study established that the 1300 nanometer wavelength laser could safely be used even when focused along the visual axis.

Experiment #2

Transmission Of The 1300 Nanometer Wavelength Beam Of The P/V YAG Laser In Various Media First, as a calibration technique, the transmission of the P/V YAG laser beam in air was measured by directing a series of 25 milli-Joule pulses at a photoelectric plate.

After this measurement was made, the absorption of each of the following media was evaluated: water, normal saline, vitreous, and albumen (egg white). Each material was placed in a series of cells placed between the laser output and the photoelectric plate and irradiated with the pulsed P/V YAG laser (wavelength =1300 nanometers). These cells had thicknesses varying from 5 to 20 millimeters.

All materials behaved similarly in these tests, indicating that the absorption characteristics were due principally to the presence of water in the media. It was further shown that a thickness of 20 millimeters of water, or the equivalent, absorbed virtually all of the laser radiation.

Experiment #3

Effect Of The 1300 Nanometer Wavelength Laser Upon The Cornea

These studies were conducted in vitro using rabbit, pig and monkey eyes which had previously been enucleated and in vivo using the eyes of rabbits placed under general anesthesia by ketamine.

The laser was focused on the front of each eye by means of a +20 diopter lens. After irradiation, the corneas were excised approximately 2 to 3 millimeters behind the limbus. Next, the endothilium was stained with trypan blue and alizarium red in accordance with the method of Spence and Peyman. Selected specimens were then fixed in 2% formaldehyde and glutaraldehyde. Following fixation overnight, the specimens were dehydrated in alcohol and then embedded in paraffin. The tissue thus prepared was cut with a microtome, stained with hematoxyline and eosin and studied under a light microscope.

Corneas which had been irradiated in front of the focal point of the beam showed no damage to the corneal stroma or to the endothilium. However, in those corneas irradiated at the focal point of the beam, the incidence of the beam upon the cornea-air interface had resulted in a spark, due to plasma formation, and in a clearly audible shock wave.

The tissue studies showed that on a clear cornea, only minimal damage was caused by irradiation by between 10 and 20 pulses. In contrast, greatly enhanced absorption effects were observed where a moderate haze existed in the epithelium or in the stroma. Where corneal damage was observed, the reactions were highly variable, ranging from modest damage to the epithelium to substantial damage to the stroma. Corneal perforation often resulted from repeated exposure to the laser pulse. When damage extended to between one-half and two-thirds of the stromal thickness, damage to the endothelium was also observed.

These findings were confirmed by histological sectioning of the studied tissues.

This study confirmed that the 1300 nanometer wavelength laser could be utilized for the treatment of intraocular tissues, membranes and fluids without substantial corneal damage, provided that the cornea itself contained no more than a minimal amount of haze.

Experiment #4

Effect Of The 1300 Nanometer Wavelength Laser Upon The Iris

Exposure of the iris to the focused 1300 nanometer laser beam resulted in damage ranging from moderate pitting of the tissue surface to tissue rupture, with accompanying hemorrhage and external gas bubble formation.

No damage to the cornea was observed as a result of these procedures, except when the focus of the laser beam was at the periphery of the iris in an eye having a hazy cornea. This phenomenon, one which has been reported by Van der Zypen et al., *Advances In Ophthalmology*, vol. 39, pp. 59-180 (1979), led to the conclusion that plasma formation can occur slightly in front of the focal point of the beam, but only when there is sufficient haze in the tissue forward of the focal point to result in absorption of the beam.

In this experiment it was shown that photocoagulation treatment of the iris may successfully be completed with the 1300 nanometer wavelength laser so long as the beam may be focused through a portion of the cornea which will not absorb any substantial part of the laser energy.

Experiment #5

Effect of the 1300 Nanometer Wavelength Laser Upon the Lens

The laser beam was focused upon the lens in two different fashions. In some instances the beam was focused through the cornea and anterior chamber, while in the others the cornea was removed before irradiation.

This study, using clear lenses, demonstrated that the lens could not be damaged by the beam. The only exception to this finding occurred when the laser was focused at the pupillary margin, in which case the lens absorbed a portion of the resulting shock wave and was caused to rupture.

The utility of the 1300 nanometer wavelength laser for disrupting occluding membranes in the vitreous and for removing other foreign bodies from the vitreous is clearly shown by this study, inasmuch as the lens is shown to be transparent to laser radiation at this wavelength.

Experiment #6
Efficacy Of The 1300 Nanometer Wavelength Laser For Capsulotomies For this study, secondary membranes were produced in pigmented eyes of rabbits and in the eyes of cynomolgus monkeys by performing extra-capsular extraction of the lens. During this procedure, two of the monkey eyes were fitted with a J-loop type of intraocular lens.

Approximately one to two months after the above procedure, each eye was irradiated with the laser, successfully rupturing the membrane in each case. The reaction to the laser beam ranged from minimal rupture of thick membranes, accompanied by gas bubble formation, to complete tissue loss.

Neither of the intraocular lenses was damaged.

The results of this experiment confirm the utility of the 1300 nanometer wavelength laser for treatments involving the removal of membranes which obstruct the passage of light to the retina (occluding membranes). Moreover, this method of removal has been demonstrated to be useful whether or not the natural or a prosthetic lens is present.

Experiment #7
Effect Of The 1300 Nanometer Wavelength Laser On The Retina Initial attempts to focus the laser beam upon the retina by means of a standard or modified contact lens were unsuccessful, inasmuch as the surfaces of such lenses were damaged by the beam. Accordingly the study was conducted by directing the beam into the eyes either through the cornea or after removal of the cornea.

It was found to be impossible to produce a retinal lesion, either in this study or in Experiment #6 above, with the laser emitting radiation having a wavelength of 1300 nanometers.

This study confirmed the preliminary finding of Experiment #1 that the 1300 nanometer wavelength laser is essentially harmless to the fundus.

Experiment #8
Effect Of The 1300 Nanometer Wavelength Laser On Methyl Methacrylate Two types of intraocular implants were examined in this study, one which contained ultraviolet-absorbing material and one which did not. The particular devices used were manufactured by the Cilco Company.

The implants were irradiated by placing them in front of the focal point of the laser beam, slightly in front of the focal point, and at the focal point. Those placed in front of the focal point suffered no damage, while those placed at or slightly in front of the focal point showed varying degrees of damage.

The above-described studies have shown that the method of treatment of the eye using the 1300 nanometer wavelength Nd:YAG laser overcomes the serious drawbacks inherent in previous laser surgical methods.

The method of the invention enables the surgeon to perform a variety of membranectomy and photocoagulation procedures without causing damage to the cornea (except in the circumstances heretofore described), without damage to the natural or prosthetic lens (with the one exception noted) and without any damage whatsoever to the retina and its associated structures, regardless of the degree of exposure of the fundus to the laser radiation. Accordingly, capsulotomies, secondary membrane treatments and the other procedures herein described may, by the method of the present invention, be successfully performed without any substantial risk of visual impairment.

While the method of the present invention has been described with reference to various preferred forms thereof and with reference to the use of certain surgical procedures and equipment, it is to be understood that the full scope of our invention is defined by the following claims.

We claim:

1. A method of laser surgical treatment of the eye comprising the steps of aiming a source capable of producing laser radiation, a major portion of which has a wavelength of from about 1100 nanometers to about 1350 nanometers or from about 1850 nanometers to about 2050 nanometers, at the intraocular tissue to be treated and thereafter exposing said tissue to said laser radiation for a time sufficient and at an intensity sufficient to induct photocoagulation or membrane disruption of said tissue whereby the surgical method is effected.

2. A method of laser surgical treatment or disruption of intraocular tissue anterior to the fundus of the eye, comprising the steps of exposing said tissue to laser radiation having a wavelength such that an amount greater than about 80% of said laser radiation is absorbed by the vitreous before reaching the fundus and inducing photocoagulation or membrane disruption of said tissue with said laser radiation whereby the surgical method is effected.

3. A method according to claim 2 wherein said laser radiation has a wavelength of from about 1100 nanometers to about 1350 nanmeters.

4. A method according to claim 2 wherein said laser radiation has a wavelength of from about 1850 nanometers to about 2050 nanometers.

5. A method according to claim 3 or claim 4 wherein said laser radiation is produced by a laser apparatus employing a neodynium-doped yttrium-aluminum garnet crystal.

6. A method according to claim 5 wherein said laser apparatus is mode-locked.

7. A method according to claim 2 wherein said laser radiation is directed into the eye in a series of pulses.

8. A method according to claim 7 wherein each of said pulses of laser radiation has a strength of from about 100 milli-Joules to about milli-Joules.

9. A method according to claim 7 wherein each of said pulses of laser radiation has a duration of from about 10 to about 50 nanoseconds.

10. A method of laser surgical treatment or disruption of intraocular tissue anterior to the fundus of the eye while reducing damage to the fundus caused by undesired penetration of laser radiation beyond the tissue to be treated, comprising the steps of exposing said tissue to a series of pulses of laser radiation having a wavelength of from about 1100 nanometers to about 1350 nanometers, said radiation being produced by an apparatus employing a neodymium-doped yttrium-aluminum garnet crystal, and said pulses havin a strength of from about 100 milli-Joules to about 150 milli-Joules and having a duration of from about 10 to about 50 nanoseconds and inducing photocoagulation or membrane disruption with said laser radiation whereby the surgical method is effected.

11. A method according to claim 10 wherein said laser radiation has a wavelength in the range of from about 1300 nanometers to about nanometers.

12. A method according to claim 10 wherein said laser apparatus is mode-locked.

13. An ophthalmic laser surgical method for treating or disrupting intraocular tissue anterior to the fundus of the eye while reducing the likelihood of photocoagulation damage to the funuds, comprising the steps of directing at said intraocular tissue laser radiation having a wavelength of from about 1100 nanometers to about 1350 nanometers of from about 1850 nanometers to about 2050 nanometers and inducing photocoagulation or membrane disruption with said laser radiation whereby the surgical method is effected.

14. A method of disrupting an intraocular membrane comprising directing at said membrane laser radiation having a wavelength of from about 1100 nanometers to about 1350 nanometers and inducing intraocular membrane disruption with said laser radiation whereby said method of disrupting said intraocular membrane is effected.

15. A method according to claim 14 for disrupting a pupillary membrane comprising directing at said membrane laser radiation having a wavelength of from about 1100 nanometers to about 1200 nanometers.

16. A method according to claim 14 for disrupting a vitreous membrane comprising directing at said membrane laser radiation having a wavelength in the range of about 1300 nanometers to about 1310 nanometers.

* * * * *